(12) United States Patent  
Sievers

(10) Patent No.: US 9,775,708 B2
(45) Date of Patent: Oct. 3, 2017

(54) HEART VALVE PROSTHESIS

(71) Applicant: Hans-Hinrich Sievers, Kronshagen (DE)

(72) Inventor: Hans-Hinrich Sievers, Kronshagen (DE)

( * ) Notice: Subject to any disclaimer, the term of this patent is extended or adjusted under 35 U.S.C. 154(b) by 8 days.

(21) Appl. No.: 14/429,554

(22) PCT Filed: Sep. 19, 2013

(86) PCT No.: PCT/EP2013/069486
§ 371 (c)(1),
(2) Date: Mar. 19, 2015

(87) PCT Pub. No.: WO2014/044762
PCT Pub. Date: Mar. 27, 2014

(65) Prior Publication Data
US 2015/0272738 A1   Oct. 1, 2015

(30) Foreign Application Priority Data
Sep. 19, 2012   (DE) .................. 10 2012 216 742

(51) Int. Cl.
    A61F 2/24      (2006.01)
(52) U.S. Cl.
    CPC .......... *A61F 2/2445* (2013.01); *A61F 2/2403* (2013.01); *A61F 2/2409* (2013.01); *A61F 2230/0063* (2013.01)
(58) Field of Classification Search
    CPC ........................... A61F 2/2403; A61F 2/2409
    USPC .......................... 623/2.2, 2.21–2.29
    See application file for complete search history.

(56) References Cited

U.S. PATENT DOCUMENTS 4,655,772 A   4/1987   De Liotta et al.
6,228,112 B1  5/2001   Klootz et al.

FOREIGN PATENT DOCUMENTS

EP      1 703 865 B1    2/2010

*Primary Examiner* — David H Willse
*Assistant Examiner* — Javier Blanco
(74) *Attorney, Agent, or Firm* — McGlew and Tuttle, P.C.

(57) ABSTRACT

A heart valve prosthesis has an annular body (2) and with several flap elements (4) which are movably connected to the annular body (2) via joints (10). The joints (10) engage on the flap elements (4) at their ventricular surface (18).

8 Claims, 3 Drawing Sheets

HEART VALVE PROSTHESIS

CROSS REFERENCE TO RELATED APPLICATIONS

This application is a United States National Phase Application of International Application PCT/EP2013/069486 filed Sep. 19, 2013 and claims the benefit of priority under 35 U.S.C. §119 of German Patent Application DE 10 2012 216 742.0 filed Sep. 19, 2012, the entire contents of which are incorporated herein by reference.

FIELD OF THE INVENTION

The invention relates to heart valve prosthesis with an annular body and with several flap elements which are movably connected to the annular body via joints.

BACKGROUND OF THE INVENTION

A heart valve prosthesis comprising an annular body which is sewn to the tissue at its outer periphery and carries several movable flap elements on its inner periphery is known from EP 1 703 865 B1. Thereby, the flap elements are articulately mounted at their side edges. The joints are thereby formed at the annular side on projections which extend into the inside of the annular body. The disadvantage of this design is the fact that regions, through which blood does not flow and at which deposits can form are present in the region of these joints.

SUMMARY OF THE INVENTION

With regard to this problem, it is an object of the invention, to provide an improved heart valve prosthesis which has a reduced risk of undesired deposits.

The heart valve prosthesis according to the invention is a mechanical heart valve prosthesis and comprises an annular body which preferably on an annular body outer periphery comprises a sewing ring for sewing the annular body to the surrounding tissue. Several flap elements are movably mounted in the annular body forming a fixed structure. For this, the flap elements are movably connected to the annular body via joints. The joints permit a pivot movement of the flap elements between a closed position, in which the several flap elements preferably bear on one another, and an opened position, in which the flap elements are directed essentially in the flow direction of the blood and release the interior of the annular body. The flap elements are preferably arranged on the joints such that they are each pivotable about a pivot axis which extends normally to the flow direction and preferably in a chord-like manner in the annular body. Thereby, the pivot axes preferably each extend such that they extend transversely, i.e. in particular normally to a symmetry axis of each flap element. The flap elements are preferably formed symmetrically to a symmetry axis extending radially to the middle point of the heart valve prosthesis. The pivot axis of the flap element preferably extends normally to this symmetry axis. Three flap elements are preferably provided, wherein then the three pivot axes of the three flap elements preferably span an equilateral triangle, wherein the tips of the triangle are each situated on the axis of symmetry of an oppositely situated flap element. The axes of symmetry of the three flap elements intersect in the middle point of the heart valve prosthesis. With this arrangement of the pivot axes, the flap elements pivot open in the radial direction departing form this middle point. I.e. the tip of each flap element which is situated at the middle point pivots on a circular path about the pivot axis, which is situated in a plane which intersects the middle axis of the heart valve prosthesis and extends parallel to this. The axis of symmetry of each flap element is simultaneously situated in this pivot plane.

According to the invention, one envisages the joints engaging on the flap elements at their ventricular surface. The ventricular surface is thereby that flap surface, onto which blood flows in its flow direction, which is to say the surface which is situated upstream in the flow direction of the blood and which faces the ventricle. The arrangement of the joints exclusively at the ventricular or systolic side, i.e. the side, onto which the blood flows in a direct manner for opening the heart valve, has the advantage that the joint regions are subjected to a complete through-flow or peripheral flow by the blood, so that no deposits are able to form in the region of the joints. The aortal surface of the flap elements which is away from the ventricle in contrast is free of components or constituents of the joints.

The joints engage on the flap elements preferably in each case in a manner distanced to their side edge or peripheral edge on the ventricular surface. This has the advantage that the edges of the flap elements are free from joints, so that blood can also freely flow over the edges in the opened condition of the heart flap and no deposits are able to form in this region. In particular, each flap element with this design preferably comprises joints which are independent of the joints of the remaining flap elements. This permits the joints and the structures carrying the joints as a whole to be designed in a slimmer manner, so that there are least undercuts and dead spaces, through which blood does not flow and in which deposits could accumulate. Thus, as a whole, one preferably succeeds in all regions of the heart valve prosthesis being directly subjected to through-flow by blood in the opened condition of the flap elements, so that no deposits can form.

The flap elements are each further preferably fastened on the annular body with two joints. The pivot axis of the flap elements thereby extends through both joints. It is ensured by way of both joints that the flap elements only pivot about this one pivot axis in a defined manner. Preferably, the two joints are arranged symmetrically on the flap element, i.e. symmetrically on both sides of a middle or symmetry axis of the flap element. The axis of symmetry preferably extends in the radial direction to the middle point or to the tip of the flap element which is situated at the middle point of the heart valve prosthesis in the closed condition. Both joints are moreover preferably distanced equally far from the annular body. The use of two joints per flap element is particularly advantageous if the joints are designed as ball joints, so that both joints together can fix the defined pivot axis. However, it is also conceivable to apply only one joint per flap element if this preferably permits a pivot movement only about one defined pivot axis.

According to a preferred embodiment, the joints in each case comprise a joint head which is attached on the annular body and which engages into a joint socket formed on the ventricular surface of the flap element. These joints are particularly preferably designed as ball joints, i.e. the joint head has the shape of a ball section, and the joint socket has a corresponding concave ball shape or shape of a ball section. The joint head and the joint socket are preferably dimensioned such that the joint head engages into the joint socket in an as play-free manner as possible, but the joint socket can freely rotate or move with respect to the joint head, in order to ensure the movability of the flap element.

A lubrication by way of the blood takes place. The joint gap itself is so small that no deposits can settle there. Despite the design of the individual joints as a ball joint, it is ensured that a pivot movement is only possible about a defined pivot axis extending through both joints, due to the arrangement of two joints per flap element. A design as a ball joint however simplifies the assembly and the manufacture and ensures a permanent, easily movability of the flap elements on the joints.

The joints on the annular body side are preferably formed on projections which extend into the interior of the annular body. One succeeds in the joints themselves being situated in the interior of the annular body, in which a strong flow of blood prevails, on account of this, and therefore blood strongly flows through the joint regions, and the formation of deposits is prevented. The projections preferably have such a length that the joint which is situated on them, on a radial line running through the joint from the middle point of the heart valve prosthesis to the annular body, is distanced to the annular body by an amount which is more than a third, preferably more than half the distance between the annular body and the middle point. The projections themselves can be designed in such a narrow manner that blood flows around them in a complete manner, so that likewise no deposits can form on the rear side of the projections, seen in the flow direction of the blood. The projections are thus preferably designed as narrow webs or arms. Preferably, likewise two joints per flap element are formed on the annular body, in the case that two joints per flap element are provided, so that each joint is situated on a single projection. In the case that two joints are provided with two projections per flap element, these are preferably arranged symmetrically to one another with respect to the axis of symmetry of the flap element. I.e. the joints and projections are designed equally and in particular mirror-symmetrically to one another. However, it is also conceivable to arrange several joints on a common projection. In the case that only one joint per flap element is provided, accordingly preferably also only one projection would be provided, on which this joint is arranged.

According to a preferred embodiment of the invention, the projections, on which the joints are situated, do not extend in a plane normal or perpendicular to the longitudinal axis of the heart valve prosthesis, wherein the longitudinal axis corresponds to the flow direction. Preferably, in contrast the projections extend at an acute angle to this longitudinal axis, i.e. at an angle <90°. One succeeds in these projections likewise extending in an angled manner to the plane spanned by the flap elements, in the closed condition of the heart valve prosthesis, by way of this. Thus, it is indeed in the vicinity of the annular body that a greater distance between the projections and the flap elements can be achieved, so that no deposits between the projections and the flap elements can form in this region. The projections particularly preferably come into contact exclusively with the joints with the flap elements.

The projections preferably extend essentially radially from the annular body into its interior, i.e. in a direction transverse to the flow direction of the blood. Preferably, the projections have a streamline cross section which favors the peripheral flow of the blood. Thereby, the cross-sectional shape is formed such that preferably no dead region or space, in which no flow of blood prevails, forms on the surface which is at the rear side in the flow direction. Deposits on the projections are prevented in this manner.

Preferably, the heart valve prosthesis according to the invention comprises at least two flap elements. With a particularly preferred embodiment, the heart valve prosthesis comprises three flap elements which are movably arranged in the annular body. Each of the flap elements is thereby preferably movably mounted in the annular body via two joints which engage on the ventricular surface of the respective flap element. The two joints of each flap element are distanced to one another in the direction of the pivot axis, so that a rotation or movement transverse to the pivot axis is prevented. Thereby, the two joints as described above are preferably arranged symmetrically, in particular mirror-symmetrically to one another. Preferably, in total six joints are provided with the arrangement of three flap elements. Each joint is preferably formed on a single web or projection which projects from the annular body radially inwards into the interior of the annular body. Thus, on the one hand a stable mounting is created and it is moreover ensured that blood flows through all regions of the heart valve prosthesis, in order to prevent deposits.

The flap elements are preferably designed and are arranged with their pivot axes in the annular body, in a manner such that on pivoting into the opened position, the flap elements do not extend beyond the outer periphery of the annular body, but always remain in the inner periphery of the annular body or in the inside of a projection of the annular body along the longitudinal axis of the heart valve prosthesis. By way of this, it is ensured that the pivoting-open into the opened position is not inhibited by way of surrounding tissue.

The flap elements are particularly preferably manufactured from carbon or as a carbon structure. Such a material is very resistant to deposits on the surface and moreover has a high wear resistance.

The annular body is preferably manufactured of metal, for example titanium. Thereby, the annular body can be composed of several parts or however particularly preferably be designed as one piece. A single-piece design simplifies the manufacture and ensures a stable structure of the annular body. A divided or multi-part design of the annular body in contrast can be advantageous with regard to the assembly of the flap elements.

The invention is hereinafter described by way of example and by way of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 5:
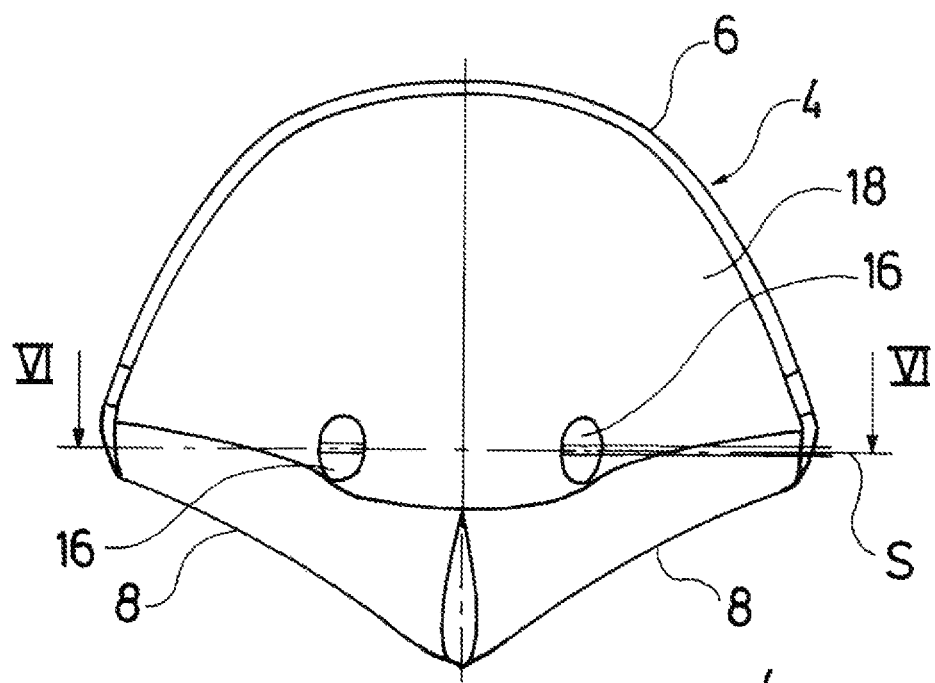
FIG. 5 is an enlarged view of a single flap element.

The mechanical heart valve prosthesis which is shown in the figures comprises an annular body 2 with three flap elements 4 which are arranged therein. An outer periphery of the annular body 2 comprises a sewing ring for sewing the annular body to the surrounding tissue. The flap elements 4 are arranged in the free interior of the annular body 2 and are articulately mounted in the annular body 4, so that they can pivot about the pivot axes S between the closed position shown in FIG. 1 and the open position shown in FIG. 2. The flap elements 4, 6 (see FIG. 5) in the closed condition shown in FIG. 1 bear on the inner periphery of the annular body 2 and bear on one another with both their inner side edges 8 running at an angle to one another, so that they close and seal the free interior of the annular body 2. In the opened condition, the flap elements 2 extend essentially in the flow direction X of the blood so that they release the interior of the annular body 2.

The individual flap elements 4 are each articulately mounted on the annular body 2, on two joints 10. The joints 10 on a ring side (an outer periphery side) comprise a ball head 12 which is arranged at the end of a web or projection 14. The projections 14 are designed as one piece with the annular body 2 and extend from the remainder of the one piece annular body 2 essentially inwards in the radial direction into the interior of the annular body 2, so that the ball heads 12 formed at the free ends of the projections 14 are situated in a distanced manner to the inner periphery of the annular body 2. The radial distance of the ball heads 12 to the inner periphery of the ring is preferably more than a third of the radius of the annular body 2 or a radial line from the middle point X through the ball head 12 to the annular body, and preferably the ball heads 4 lie at roughly half the radius.

Figure 4:
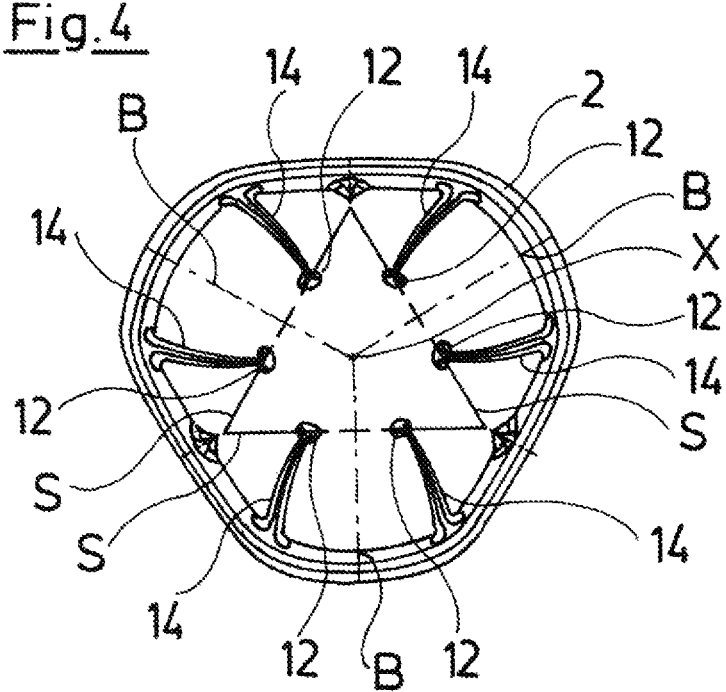
FIG. 4 is a plan view of the annular body without flap elements.
Figure 6:
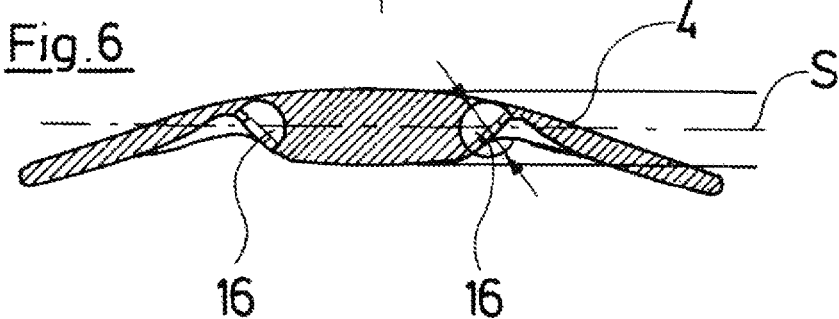
FIG. 6 is a sectioned view of the flap element according to FIG. 5, along the line VI-VI in FIG. 5.

The two projections 14 which belong to (associated with) each flap element 4, and their ball heads 12 are distanced to one another in the direction of the pivot axis S. Thereby, the flap elements 4 and their two associated projections 14 are each formed symmetrically to the axes of symmetry B. This means that the two projections 14 with the ball bodies 12 of each flap element 4 are arranged mirror-symmetrically to an axis of symmetry B. The three symmetry axes B of the three flap elements 4 intersect in the middle point or the longitudinal axis X which corresponds to the flow direction (see FIG. 4). The pivot axis S of each flap element 4 extends through the associated two ball heads 12, i.e. through the two joints 10. The ball heads 12 engage on the flap elements 4 in joint sockets 16 which are likewise designed in a ball-shaped manner i.e. have the shape of a ball section, as is shown in FIG. 6. The ball heads 12 which are likewise designed in the shape of a ball section, and the joint sockets 16 are preferably designed such that they can engage into one another essentially without play, wherein the movability of the flap elements 4 about the pivot axis S is retained. Thus, a very narrow and or thin joint gap is ensured between the ball head 12 and the joint socket 16, in which no deposits can form. The ball heads 12 with the projections 14 and the annular body 2 are preferably designed in a single part manner of metal, for example titanium. The flap elements 4 can likewise be designed of, in particular formed of, metal, as the case may be with suitable coatings. The flap elements 4 however are preferably formed of a carbon structure which on the one hand gas a high wear resistance and on the other hand has a surface, on which essentially no deposits form.

Figure 1:
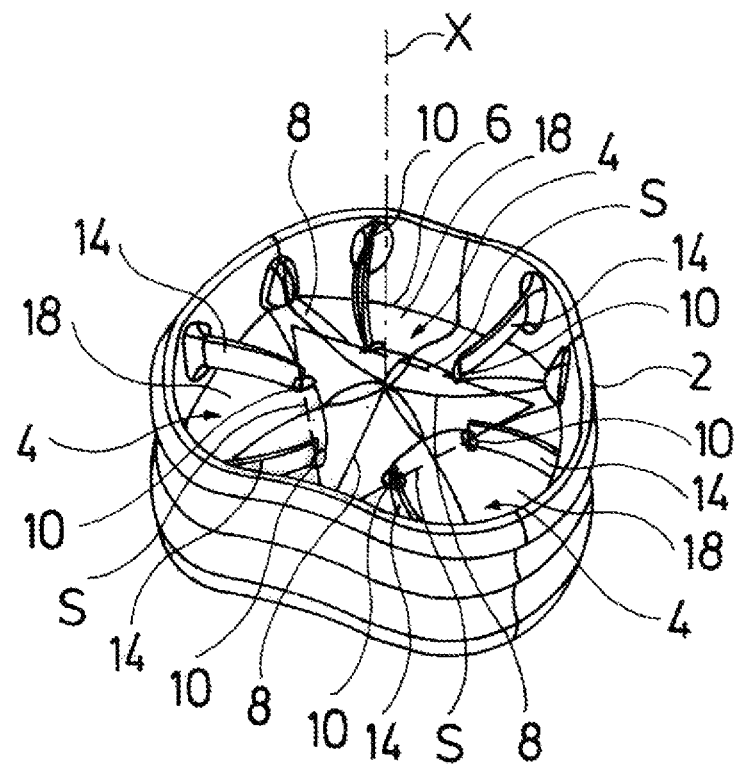
FIG. 1 is a perspective entire view of a heart valve prosthesis according to the invention, in the closed condition.
Figure 2:
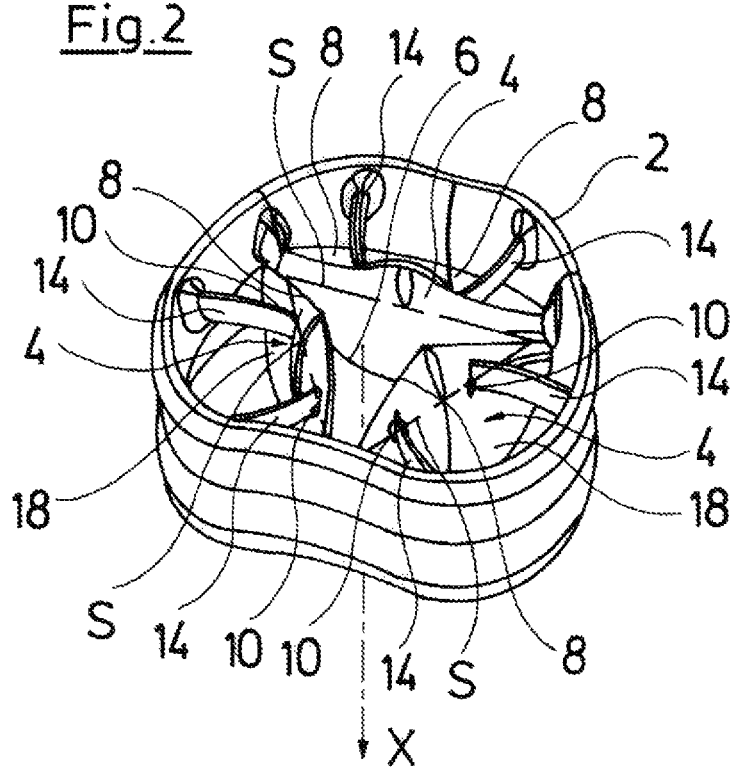
FIG. 2 is a perspective entire view of a heart valve prosthesis according to the invention and according to FIG. 1, in the opened condition.
Figure 3:
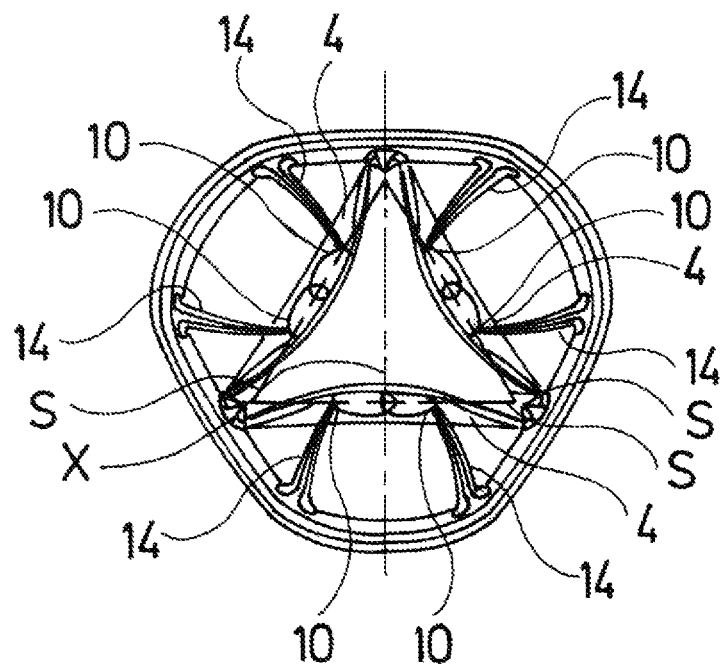
FIG. 3 is a plan view of the heart valve prosthesis according to FIG. 2, in the open condition.

As is shown in FIGS. 1 and 2, the joints 10 are situated on the ventricular side or surface 18 of the flap elements 4 which is upstream in the envisaged flow direction of the blood along the longitudinal axis X through the heart valve prosthesis and which faces the ventricle. The ventricular surface 18 is thereby that surface of the flap elements 4, onto which the blood flows in the flow direction X. The joints 10 or the joint sockets 16 of the joints 10 on the flap elements 4 are moreover situated distanced to the side edges 6 and 8 in the central region of the flap elements 4. With this design, one succeeds in the joints 10 lying completely in the flow and thus being subjected to through-flow such that deposits can neither accumulate in the joints 10 nor on the projections 14 which carry the joints 10 on the ring side. As is to be recognized in FIG. 4, the projections 14 have a streamline or flow-optimized cross section which is formed such that the webs, seen in the flow direction X are designed in a very narrow manner and, seen in the flow direction X, essentially form no dead spaces on their rear side, in which dead space deposits could form.

The projections 14 in this example extend at an acute angle to the longitudinal direction X, so that the projections 14 only come into contact with the flap elements 4 with their ball heads 12. In particular, the projections 14 do not bear on the surface of the flap elements 4 in the closed position, as is to be seen in FIG. 1. Thus, deposits are prevented from being able to form in this region.

While specific embodiments of the invention have been shown and described in detail to illustrate the application of the principles of the invention, it will be understood that the invention may be embodied otherwise without departing from such principles.

The invention claimed is:
1. A heart valve prosthesis comprising:
an annular body with a first axial end and a second axial end;
a plurality of joint heads connected to said annular body;
a plurality of flap elements arranged in an interior of the annular body, each of said plurality of flap elements having a radially outside edge, a radially inside edge, a ventricular surface adapted to face a ventricle of a heart and an aortal surface diametrically opposite said ventricular surface, each of said flap elements defining two joint sockets formed on the ventricular surface, each of said joint heads engaging with one of said joint sockets to pivotally connect said plurality of flap elements to said annular body, said joint heads and said joint sockets pivotally mounting said flap elements between an open position allowing flow through said annular body and a closed position blocking flow through said annular body, said joint heads and said joint sockets being arranged to move said flap elements into said open position when flow through said annular body is in a flow through direction from said first axial end to said second axial end of said annular body, said joint heads and said joint sockets being arranged to move said flap elements into said closed position to a flow through said annular body from said second axial end to said first axial end of said annular body, said ventricular surfaces of said flap elements being an upstream side with respect to said flow through direction, each of the joint sockets is distanced from the radially inside edge and from the radially outside edge of the respective flap element; and a plurality of elongated projections extending radially inward from said annular body and into the interior of the annular body, each of the joint heads being formed on a radially inward end of one of said projections, each of said flap elements being connected to said annular body through two respective said projections, wherein each of said joint heads and said joint sockets being arranged exclusively at the ventricular surface of the respective flap element, and wherein the aortal surfaces of the flap elements are devoid of any joints, wherein said radially outside edge of each of said flap elements moving downstream with respect to said flow through direction when said flap elements move from said closed position to said open position, and said radially inside edge of each of said flap elements moving upstream with respect to said flow through direction when said flap elements move from said closed position to said open position.

2. A heart valve prosthesis according to claim 1, wherein: wherein the two joint heads engage into the two joint sockets on the respective flap element in a symmetrical manner.

3. A heart valve prosthesis according to claim 1, wherein the projections have a streamline cross section.

4. A heart valve prosthesis according to claim 1, wherein at least three flap elements are arranged in the annular body.

5. A heart valve prosthesis according to claim 1, wherein the flap elements are manufactured of carbon.

6. A heart valve prosthesis according to claim 1, wherein the annular body is manufactured of metal.

7. A heart valve prosthesis according to claim 1, wherein the annular body is designed as one piece.

8. A heart valve prosthesis according to claim 1, wherein: each of said joint sockets is a blind bore with an opening of said blind bore being in said respective ventricular surface.

\* \* \* \* \*